United States Patent [19]
Cline et al.

[11] Patent Number: 5,443,068
[45] Date of Patent: Aug. 22, 1995

[54] MECHANICAL POSITIONER FOR MAGNETIC RESONANCE GUIDED ULTRASOUND THERAPY

[75] Inventors: Harvey E. Cline, Schenectady; Kenneth W. Rohling, Burnt Hills; Walter R. Abeling, Amsterdam, all of N.Y.

[73] Assignee: General Electric Company, Schenectady, N.Y.

[21] Appl. No.: 312,247

[22] Filed: Sep. 26, 1994

[51] Int. Cl.6 .............................................. A61B 5/055
[52] U.S. Cl. ................................ 128/653.5; 128/653.2; 601/3; 607/97
[58] Field of Search ............... 128/653.2, 653.5, 660.03; 601/2-4; 607/96, 97

[56] References Cited

U.S. PATENT DOCUMENTS

| | | | |
|---|---|---|---|
| 4,684,894 | 8/1987 | Bliehall | 128/653.5 |
| 4,791,371 | 12/1988 | Krol | 128/653.5 |
| 5,042,487 | 8/1991 | Marquardt | 128/653.2 |
| 5,131,392 | 7/1992 | Jolesz et al. | 128/653.2 |
| 5,247,935 | 9/1993 | Cline et al. | 128/653.2 |
| 5,275,165 | 1/1994 | Ettinger et al. | 128/653.2 |
| 5,291,890 | 3/1994 | Cline et al. | 128/653.2 |
| 5,307,812 | 5/1994 | Hardy et al. | 128/653.2 |
| 5,368,032 | 11/1994 | Cline et al. | 128/653.2 |

*Primary Examiner*—Krista M. Zele
*Attorney, Agent, or Firm*—Lawrence P. Zale; Marvin Snyder

[57] ABSTRACT

A positioner for a magnetic resonance (MR) surgery system which positions a focal point of an ultrasound transducer to selectively destroys tissue in a region within a patient. The positioning means moves an ultrasound transducer under the control of an operator. Mechanical threaded shafts and slides act as screw drives causing several connected slides to move the ultrasound transducer in three dimensions. Expanding shafts are connected between a fixed point on a housing and the actuating point of the threaded shafts. Two of the expanding shafts employ universal joints allowing the shafts to rotate as they follow the slides. The third expanding shaft need only expand but the relative angle between its attachment points does not change, thereby eliminating the need for universal joints. An MR imaging system employing a temperature sensitive pulse sequence, creates an image of the tissue and the region being heated to allow the operator to adjust the position of the ultrasonic transducer so as to direct ultrasonic energy to the appropriate location.

4 Claims, 5 Drawing Sheets

MECHANICAL POSITIONER FOR MAGNETIC RESONANCE GUIDED ULTRASOUND THERAPY

BACKGROUND OF THE INVENTION

1. Field of the Invention

The present invention relates to a system for enabling non-invasive surgery to be performed by localized heating and more particularly to a system for surgery by localized heating guided by magnetic resonance (MR) imaging.

2. Description of Related Art

Conventional Magnetic Resonance (MR) Imaging provides the radiologist with internal views of a subject's anatomy. MR Imaging provides excellent contrast between different tissues and is useful in planning surgical procedures. A tumor in a subject is much more visible in an MR image than as seen in actual surgery because the tumor and normal tissue often look similar in surgery. The tumor can also be obscured by blood during surgery. A view of the heated region is provided with the use of MR temperature sensitive pulse sequences. MR imaging temperature-sensitive pulse sequences are described in U.S. Pat. No. 5,307,812 May 3, 1994 "Heat Surgery System Monitored by Real-Time Magnetic Resonance Profiling" by C. Hardy, H. Cline which describes capturing temperature mapped imaging of a subject. Experiments on animals show that a heated zone above a critical temperature destroys tissue. Heating tissue beyond a critical temperature for a period of time causes necrosis, destruction of tissue.

Tumors have been selectively destroyed in cancer subjects using focused ultrasound heating guided by MR imaging.

MR imaging employs large magnets for creating a homogeneous magnetic field, and gradient coils for altering the magnetic field in a uniform manner in time or space, creating magnetic field gradients. MR imaging also employs radiofrequency (RF) coils for applying an RF field to tissue to be imaged, causing the tissue to resonate and create an MR response signal. The MR response signal is used to construct an image. The degree of homogeneity of the magnetic field and the linearity of a magnetic field gradient over space are important in creating a clear, undistorted image. Interference with the RF field also reduces the quality of the created image.

Recently, there is a desire to create interactive images of internal organs of a patient during surgery. Since magnetic resonance imaging provides great detail in images of soft tissues, it is advantageous to use MR imaging. The best imaging results when surgical equipment does not interfere with the magnetic and RF fields created by the MR imaging equipment.

Many metals are ferromagnetic and are physically pulled toward a magnet. Since the magnetic field employed in MR imaging is large, an amount of magnetic force applied to the equipment can be large. Equipment used near the MR magnet, therefore, should not be made of a ferromagnetic material since a magnetic force would be applied to them causing them to be difficult to manipulate.

Other problems occur with materials in which eddy currents are produced when placed in a variable magnetic field. The eddy currents in these materials, usually electrical conductors, create their own magnetic field which interferes with the fields used for MR imaging. Therefore, materials which exhibit eddy currents, such as aluminum and copper, should not be used within a changing magnetic field.

Additionally, conducting materials disturb and distort the radiofrequency electromagnetic fields necessary for resonance imaging.

The degree of magnetization the material exhibits per applied magnetic field is defined as susceptibility. The susceptibility of a material also affects the homogeneity of the applied magnetic field in a region surrounding the material. This creates large distortions in an MR image near the material.

In U.S. Pat. No. 5,247,935 Sep. 28, 1993 "Magnetic Resonance Guided Focused Ultrasound Surgery" by H. Cline, R. Ettinger, K. Rohling, R. Watkins; and U.S. Pat. No. 5,275,165 Jan. 4, 1994 "Magnetic Resonance Guided Ultrasound Therapy System With Inclined Track to Move Transducers in a Small Vertical Space" by R. Ettinger et al., assigned to the present assignee and hereby incorporated by reference, an ultrasound transducer is positioned within an MR Imaging magnet with the use of hydraulics. These positioners are MR compatible, however, these required hydraulic lines, pumps and motors, and optical position encoders which added considerable complexity and also required considerable amount of maintenance.

Currently, there is a need for a simplified device which can accurately localize heat to selectively kill or destroy tumor tissue without damage to surrounding healthy tissue while allowing MR images to be acquired.

OBJECTS OF THE INVENTION

It is an object of the present invention to position focused ultrasound equipment guided by magnetic resonance imaging. It is another object of the present invention to selectively destroy tumors with a small amount of invasiveness.

SUMMARY OF THE INVENTION

Heat from a focused ultrasound transducer is concentrated at a focal point positioned by a magnetic resonance (MR) compatible positioner, to selectively destroy tumor tissue of a patient with minimal invasiveness. The positioner is designed to function in an MR imaging apparatus allowing an operator performing the procedure, to view MR images of a region within the patient being heated. The MR images are used to monitor the tissue temperature with a diffusion sensitive pulse sequence. The positioning means has a transducer plate constructed of an MR compatible material, for carrying the energy transducer.

A first slide, also constructed of an MR compatible material, has a first threaded shaft slideably connected to the transducer plate such that the transducer plate slides relative to the first slide when the first threaded shaft is rotated.

A second slide also has a second threaded shaft slideably connected to the first slide such that the first slide slides relative to the second slide when the second threaded shaft is rotated.

A base plate has a third threaded shaft slideably connected to the second slide such that the second slide slides relative to the base plate when the third threaded shaft is rotated.

External motors and expanding shafts cause rotation of the first, second and third threaded shafts thereby causing the ultrasound transducer to be positioned in three dimensions.

The positioning means is responsive to a control unit which actuate structures to move the transducer.

BRIEF DESCRIPTION OF THE DRAWINGS

The features of the invention believed to be novel are set forth with particularity in the appended claims. The invention itself, however, both as to organization and method of operation, together with further objects, may best be understood by reference to the following description taken in conjunction with the accompanying drawing in which:

FIG. 5b is a cross sectional view of the expanding shafts of FIG. 5a.

DETAILED DESCRIPTION OF THE INVENTION

Tumor tissue in a patient can be selectively destroyed by localized heating without affecting the surrounding healthy tissue. In the present invention heat is applied to the tumor tissue.

Figure 1:
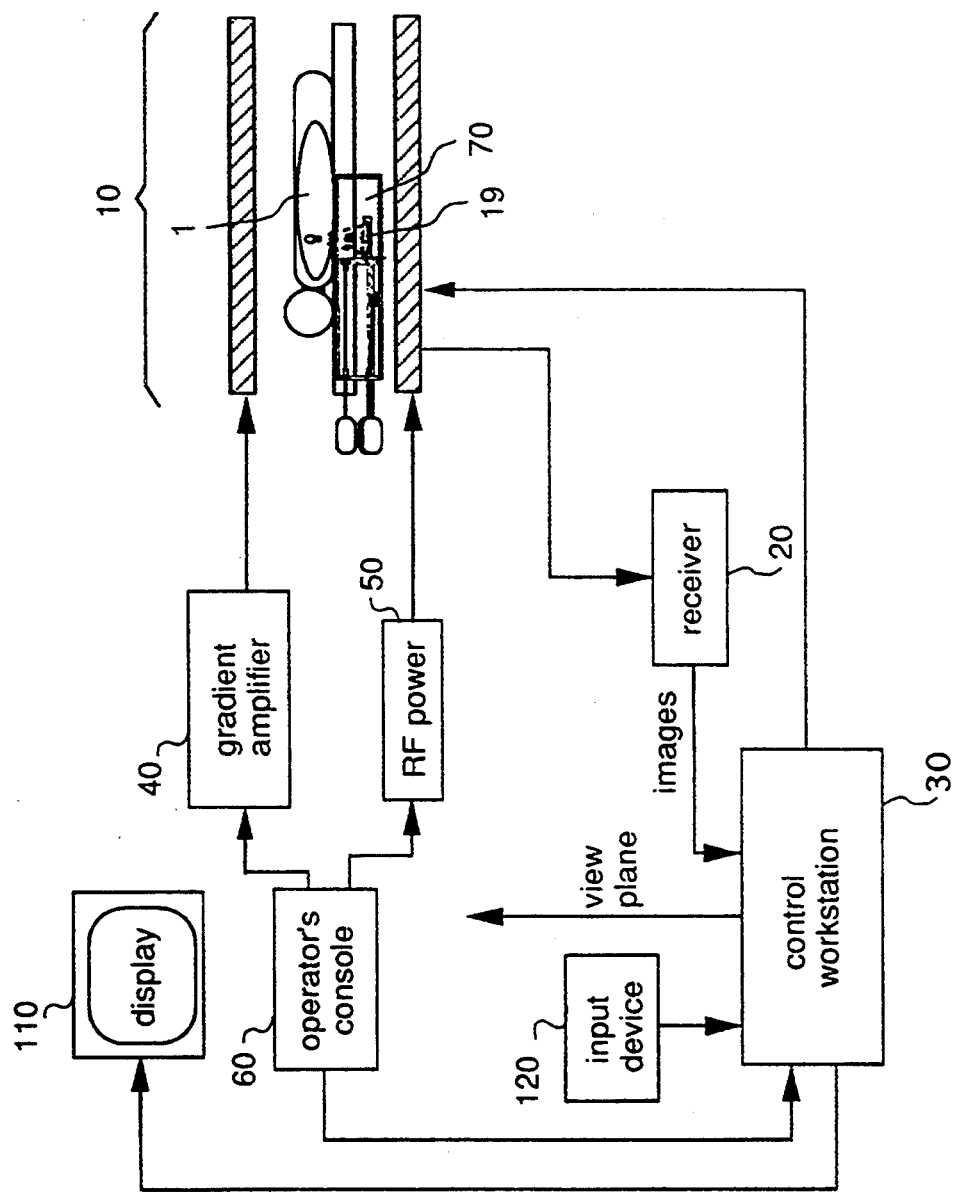
FIG. 1 is a schematic block diagram of the present invention.

A schematic block diagram of the magnetic resonance surgery system is shown in FIG. 1. A magnetic resonant (MR) imaging system 10 employs pulse sequences in the well known manner to rapidly acquire images of a patient 1. A gradient amplifier 40 and a radiofrequency (RF) power source 50 supply the power for the sequences. An operator console 60 is used to control the imaging system. Raw data is sent from receiver 20 to a control workstation 30 that displays images on a display means 110 to a surgeon. Control workstation 30 may compute a path from transducer 19 to a desired location within patient 15 which avoids bone and air spaces. The surgeon indicates the desired location of the focal point of ultrasound transducer 19 by means of an input device 120 which can be a three-dimensional pointing device such as a track ball or a mouse.

Control workstation 30 actuates a positioning means 70 to position ultrasound transducer 19. Magnetic resonant imaging system 10 then employs pulse sequences to rapidly acquire temperature sensitive images of patient 1. Since both the internal structures and heated regions are imaged, the surgeon can accurately position the heated region to correspond to a desired internal structure through input device 120.

Figure 2:
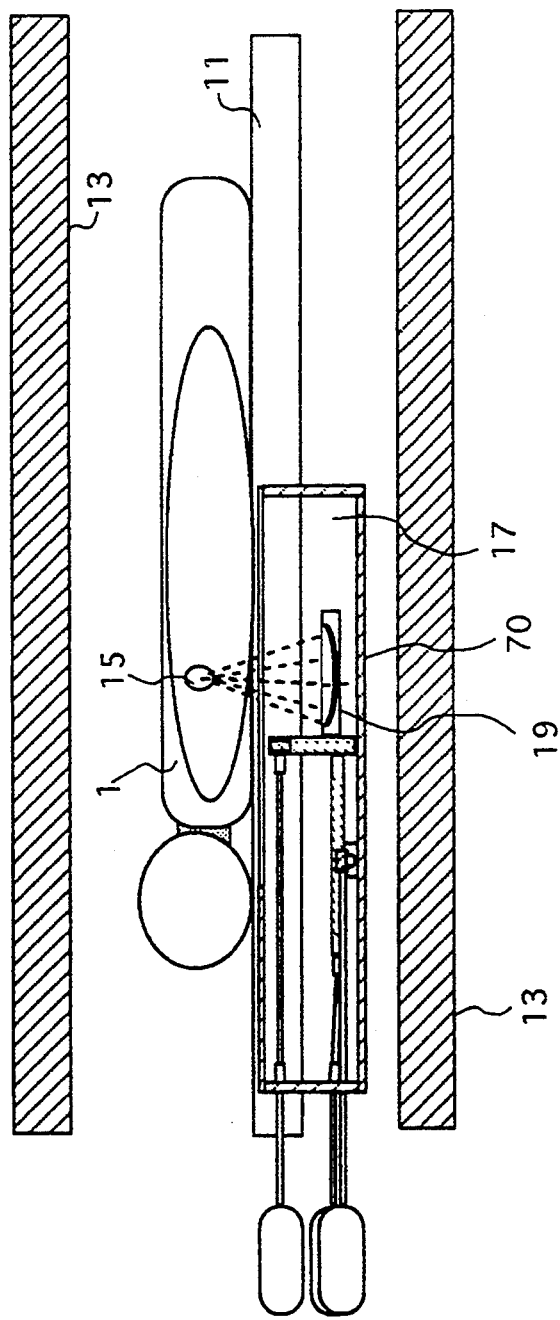
FIG. 2 is an illustration of a patient positioned for surgery within the bore of the magnets of an MR Imaging system employed in the present invention.

As shown in FIG. 2, patient 1 is placed on a table 11 designed to accommodate focused ultrasound transducer 19 in an ultrasound conducting liquid bath 17. Ultrasound conducting liquid 17 is chosen to be one that will conduct ultrasonic energy with little attenuation. Ultrasound transducer 19 can be moved inside the bore of an MR imaging magnet 13 by positioning means 70 to focus on different locations within patient 1. A path is computed by control workstation 30 from a set of images of the patient taken during surgery planning avoiding bone or air in the path of the ultrasound beam. The focal point of ultrasound transducer 19 is positioned along the computed path by positioning means 70 onto a tumor 15. The ultrasound transducer is moved while the surgeon views cross sectional temperature sensitive images.

Figure 3:
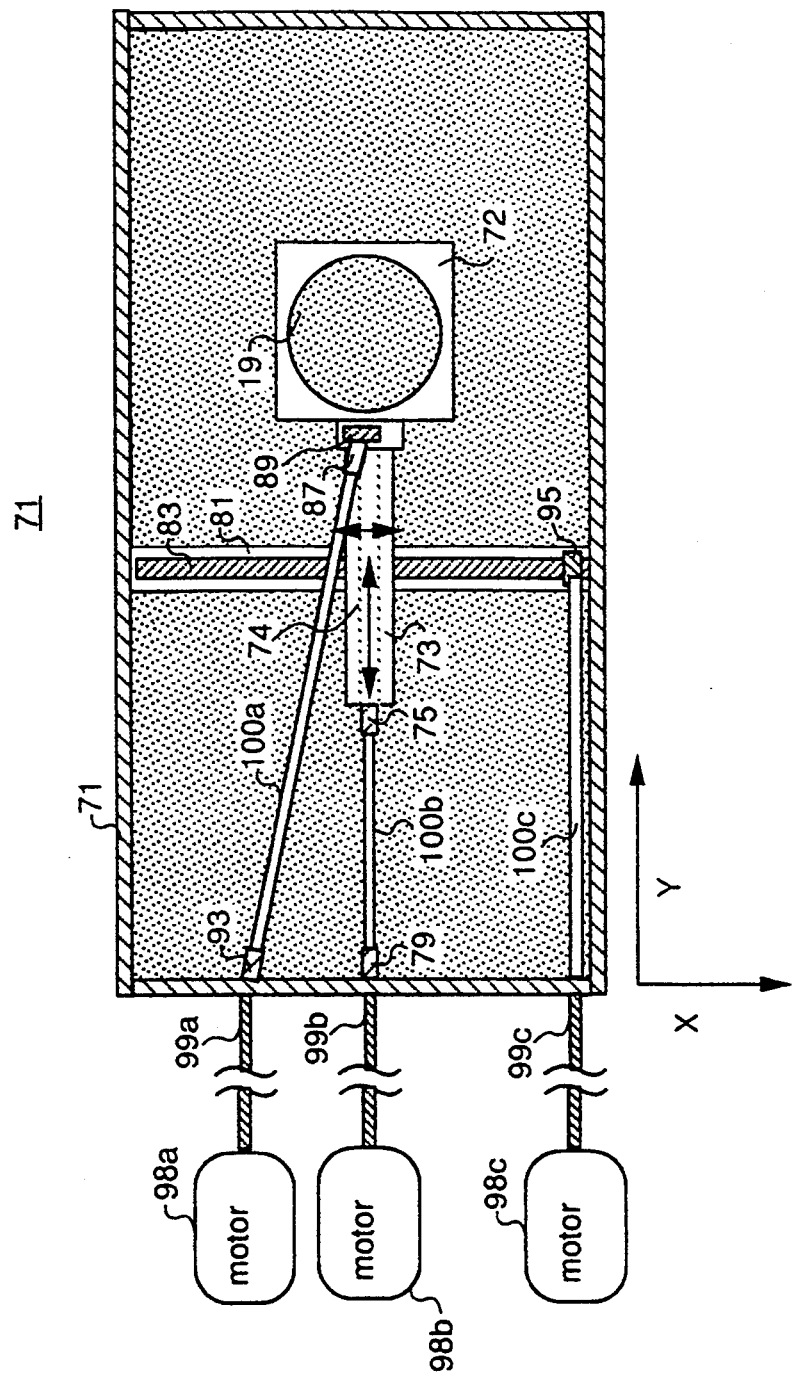
FIG. 3 is a plan view of a positioner according to the present invention.
Figure 4:
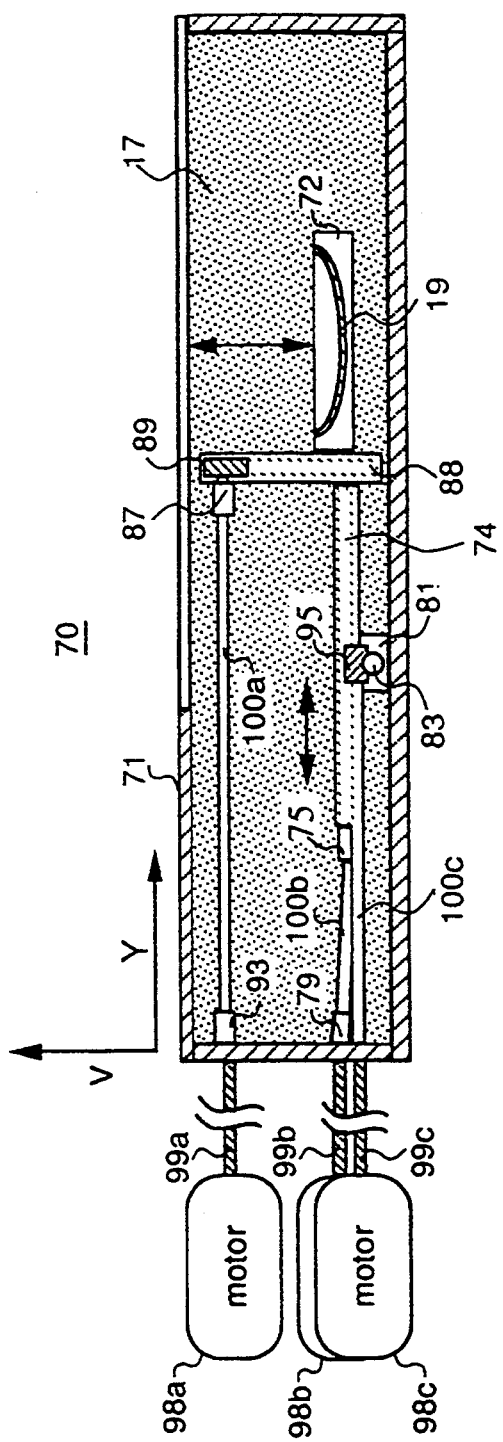
FIG. 4 is an elevational view of a positioner according to the present invention.

FIGS. 3 and 4 show a plan and elevational view of positioner 70 of FIG. 2, respectively. Transducer 19 is secured to a transducer plate 72. RF power is provided to ultrasound transducer 19 by a coaxial cable. A threaded shaft 88 driven by expanding shaft 100a and helical gear 89 cause transducer plate 72 to move in a vertical direction. Horizontal slide 73 moves in an X direction as it slides along threaded shaft 83. Threaded shaft 83 is connected to helical gear 95 which is driven by shaft 100c. Threaded shaft 83 is secured within base plate 81. A threaded shaft 74 within horizontal slide 73 is driven by expanding shaft 100b. As threaded shaft 74 rotates, horizontal slide 73 moves in the Y direction with respect to housing 71.

As transducer 19 is moved around within housing 71, the length of expanding shafts 100a, 100b changes. Also, the angle between the point of attachment on either end of the expanding shafts also changes. Since these shafts also rotate universal joints 93 and 87 are required on shaft 100a and 79 and 75 on the ends of shaft 100b.

Motors 98a, 98b and 98c connect to external shafts 99a, 99b, 99c which in turn actuate expanding shafts 100a, 100b and shaft 100c. Universal joints 93 and 79 are connected between the external shafts and expanding shafts 100a and 100b, respectively. External shafts 99a, 99b and 99c are designed to allow patient table 11 to move in and out of MR magnet 13, typically about 2 to 5 meters. Motors 98a, 98b and 98c, may be a great distance from transducer 19 and therefore outside the magnetic field used in MR imaging.

All materials used for positioner 70 are preferably made of a non-metallic and non-magnetic material since they would be employed within the magnet of an MR imaging system. The magnetic susceptibility of the materials used preferably is chosen to be similar to that of the patient being imaged. The magnetic susceptibility of materials further from transducer 19 affect the magnetic field in an imaging volume around transducer 19 less than materials close by. Since the imaging volume typically is on the order of 20 inches and the positioner has a length of approximately 30 inches and a width of 13 inches, expanding shafts 100a, 100b and shaft 100c may be made of a metallic, but non-magnetic material, and therefore produce little or no distortion in the MR image.

Figure 5A:
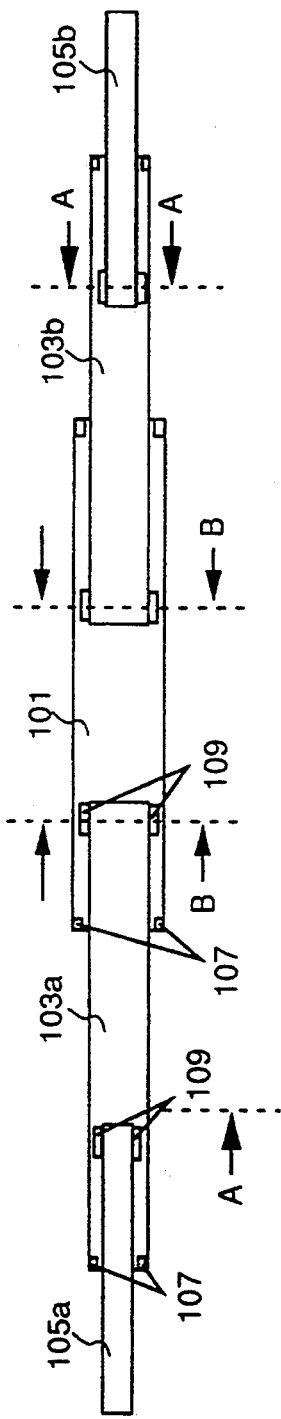
FIG. 5a is a more detailed view of the expanding shafts of FIG. 4.
Figure 5B:
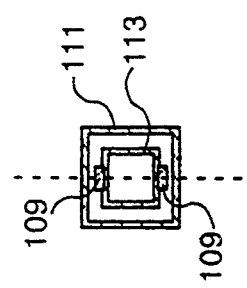

FIGS. 5a and 5b illustrate one embodiment of the expanding shafts 100a, 100b and shaft 100c. In FIG. 5a it is shown that the expanding shaft consists of a plurality of tubular telescoping sections 101, 103, 105. Each telescoping section has an enlarged protuberance 109. A stop pin 107 is located at the end of sections 101, 103a, 103b. As the sections are extended, protuberance 109 comes in contact with stop pin 107 therefore stops the sections from pulling out from inside one another.

In FIG. 5b, a cross section is shown through points A—A and B—B. The cross sections of each section in this embodiment has a square geometry. Any geometry may be used for a cross section, provided there is some means to pass torsion from one section to the next. Expanding shafts 100a and 100b allow torsional forces to be applied to threaded shafts 88, 74 and 83 causing motion of transducer plate 72, and hence ultrasonic transducer and its focal point in three dimensions within patient I to selectively heat a desired region. These may operate under the control of control workstation 30 to direct the focal point to a location indicated by the operator through input device 120.

In another embodiment, stop pins 107 of the outer section fits within a slot in the inner section thereby causing the sections to slide relative to each other up until the end of the slot without being pulled apart. The slot and pin may be reversed such that the pin is in the inner section with the slot being in the outer section.

Preferably, materials of positioning means 70 are non-metallic and non-magnetic in order to minimize any interference with the MR imaging system. The materials used in constructing the positioning means 70 have magnetic susceptibility similar to the patient being imaged. The magnetic susceptibility of structures of positioning means 70 closer to the region being imaged have more effect on image distortion than those further the region of interest.

Even though, optimally, it would be best to have all materials made of a magnetic susceptibility equal to that of the patient being imaged, external shafts 99a, 99b, 99c may be constructed of telescoping brass rods which are indexed to allow extension of patient table 11 as it is inserted and retracted from the MR magnet. Brass is non-magnetic, but metallic. The use of brass does not significant image distortion, since the external shafts are a good distance from the imaging volume. However, since the external shafts are partially within the MR magnet, there would be a great deal of force acting on them from the MR magnet if they were constructed from a magnetic material, and preferably are of a non-magnetic material.

The motors 98a, 98b, 98c may be conventional computer controlled stepping motors if located far enough outside of the magnet and imaging volume, so as not to interact with the magnetic field.

An ultrasound membrane 74 attached to casing 71 is a flexible material which is ultrasound transparent such as a Mylar plastic film diaphragm, a trademark of the E. I. du Pont Nemours and Company, Wilmington, Del. Ultrasound membrane 71 is made thin enough to conform to the contours of a patient. The patient is placed on ultrasound membrane 71 with ultrasonic conducting gel extending between the ultrasound membrane and the patient. Energy from ultrasound transducer 19 passes through fluid 17, through ultrasound membrane 74 through the ultrasound gel and into the patient. In order to efficiently transfer the energy, there should be no intervening air spaces between transducer 19 and the patient.

This results in a positioner capable of operating in an MR imaging field and moving a focused ultrasound transducer such that its focal point may be positioned in three dimensions. The present invention has several advantages over prior art hydraulic positioners such as:

a mechanical positioner according to the present invention is more tightly coupled to the motors than hydraulic systems, giving quicker response and more accurate control;

alignment of master cylinders and optical encoders are not necessary;

fabrication costs are lower for the present invention compared to the hydraulic systems; and the range of motion of the present invention is larger then that of the hydraulic positioners.

While several presently preferred embodiments of the invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) focused heat system for positioning a focal point of an energy transducer within a subject, comprising:
   a) an energy transducer for concentrating energy at a focal point;
   b) a subject interface located between the energy transducer and said subject, for facilitating energy to pass from the energy transducer to said subject;
   c) a transducer plate constructed of an MR compatible material, for carrying the energy transducer:
   d) a first slide constructed of an MR compatible material, having a first threaded shaft slideably connected to the transducer plate such that the transducer plate slides relative to the first slide when the first threaded shaft is rotated;
   e) a second slide constructed of an MR compatible material, having a second threaded shaft slideably connected to the first slide such that the first slide slides relative to the second slide when the second threaded shaft is rotated;
   f) a base plate constructed of an MR compatible material, having a third threaded shaft slideably connected to the second slide such that the second slide slides relative to the base plate when the third threaded shaft is rotated;
   g) a first actuating means for causing rotation of the first threaded shaft;
   h) a second actuating means for causing rotation of the second threaded shaft; and
   i) a third actuating means for causing rotation of the third threaded shaft thereby causing the energy transducer to be positioned in three dimensions.

2. The MR focused heat system of claim 1 wherein at least one of the first, second and third actuating means comprises:
   a) expanding shafts connected to the threaded shafts, capable of expanding or contracting to move with the threaded shafts and for providing torsional forces to the threaded shafts; and
   b) motor means functionally coupled to the expanding shafts for applying torsional forces to the threaded shafts.

3. The MR focused heat system of claim 1 wherein the subject interface comprises:
   a) an ultrasound transparent membrane in contact with the subject;
   b) an ultrasound transparent medium in contact with the membrane and situated between the membrane and the transducer, for conducting ultrasound energy from the transducer to the membrane.

4. The MR focused heat system of claim 1 further comprising:
   a) an input device allowing an operator to choose a three-dimensional position for the energy transducer; and
   b) a control workstation coupled to the input device, the first, second, and third actuating means for converting the chosen three-dimensional position to a position signal, and for driving the first, second and third actuating means to move said energy transducer to the chosen three-dimensional position.

* * * * *